(12) United States Patent
Zhang et al.

(10) Patent No.: US 8,658,972 B2
(45) Date of Patent: Feb. 25, 2014

(54) ION MOBILITY TUBE

(75) Inventors: Yangtian Zhang, Beijing (CN); Hua Peng, Beijing (CN); Xiuting Zhang, Beijing (CN); Xiaoyong Zheng, Beijing (CN)

(73) Assignee: Nuctech Company Limited, Beijing (CN)

( * ) Notice: Subject to any disclaimer, the term of this patent is extended or adjusted under 35 U.S.C. 154(b) by 0 days.

(21) Appl. No.: 13/807,973

(22) PCT Filed: May 3, 2011

(86) PCT No.: PCT/CN2011/073609
§ 371 (c)(1),
(2), (4) Date: Feb. 8, 2013

(87) PCT Pub. No.: WO2012/003739
PCT Pub. Date: Jan. 12, 2012

(65) Prior Publication Data
US 2013/0206982 A1    Aug. 15, 2013

(30) Foreign Application Priority Data
Jul. 5, 2010  (CN) .......................... 2010 1 0225133

(51) Int. Cl.
*H01J 49/26* (2006.01)
*H01J 49/40* (2006.01)
*B01D 59/44* (2006.01)

(52) U.S. Cl.
USPC ........... 250/288; 250/287; 250/286; 250/290; 250/281

(58) Field of Classification Search
USPC .......................... 250/288, 287, 286, 290, 281
See application file for complete search history.

(56) References Cited

U.S. PATENT DOCUMENTS 4,777,363 A   10/1988   Eiceman et al.
6,943,347 B1   9/2005   Willoughby et al.
(Continued)

FOREIGN PATENT DOCUMENTS

CN      201378160 Y    1/2010
DE  10 2006 006 683 A1  8/2007
JP      2005-174619 A   6/2005

OTHER PUBLICATIONS

International Search Report for PCT Application No. PCT/CN2011/073609, dated Jul. 28, 2011. 3 pages.
Written Opinion (in Chinese) for International Search Report for PCT Application No. PCT/CN2011/073609, dated Jul. 28, 2011, 4 pages.
Search Report from European Patent Application No. 11803093.1-1554/2579293, dated Oct. 18, 2013, 7 pages.

(Continued)

*Primary Examiner* — Nikita Wells
(74) *Attorney, Agent, or Firm* — Westman, Champlin & Koehler, P.A.

(57) ABSTRACT

An ion mobility tube comprises an ionization source chamber having a center ionization source chamber hole, an ion door, a mobility region unit having a center mobility tube chamber, a constraining grid, and a Faraday disk, and the ionization source chamber, the ion door, the mobility region unit, the constraining grid, and the Faraday disk are laminated together in sequence in a front-rear direction, wherein the mobility region unit comprises a first insulator and first metal electrode sheets concentrically fixed to a front surface and a back surface of the first insulator respectively. The mobility region unit comprises the first insulator and the first metal electrode sheets which are integral. Therefore, the ion mobility tube is advantageous in simplified manufacturing, and convenient for detachment and assembly.

23 Claims, 9 Drawing Sheets

(56) References Cited

U.S. PATENT DOCUMENTS

| | | | |
|---|---|---|---|
| 7,155,812 B1 * | 1/2007 | Peterson et al. | 29/610.1 |
| 7,223,969 B2 * | 5/2007 | Schultz et al. | 250/290 |
| 7,851,747 B2 * | 12/2010 | Chen et al. | 250/287 |
| 8,405,024 B2 * | 3/2013 | Li et al. | 250/286 |
| 2005/0109930 A1 | 5/2005 | Hill, Jr. et al. | |
| 2008/0073514 A1 | 3/2008 | Landgraf et al. | |
| 2009/0236514 A1 | 9/2009 | Renner | |

OTHER PUBLICATIONS

Plumlee et al., "Development of a Micro-Nozzle and Ion Mobility Spectrometer in LTCC", 0-7803-8369-9/04/$20.00 © 2004 IEEE, BNSDOCID: <XP10705323AI>, pp. 95-98, 4 total pages.

Plumlee et al., "Ion Mobility Spectrometer Fabricated in LTCC", BNSDOCID: <XP55083344AI>, 6 pages.

* cited by examiner

ION MOBILITY TUBE

CROSS-REFERENCE TO RELATED APPLICATION

This Application is a Section 371 National Stage Application of International Application No. PCT/CN2011/073609, filed 03 May 2011 and published as WO 2012/003739 A1 on 12 Jan. 2012, in Chinese, which claims the benefit of priority to Chinese Patent Application No. 201010225133.0, filed on Jul. 5, 2010 in the Chinese Intellectual Property Office, the contents of which are hereby incorporated by reference in their entirety.

BACKGROUND OF THE INVENTION

1. Field of the Invention

The present invention relates generally to a detection apparatus based on ion mobility principles for trace detection, and in particular to an ion mobility tube.

2. Description of the Related Art

The ion mobility tube is a core part of a detection apparatus based on the ion mobility principles. It generally comprises an ionization source chamber, an ion door, a mobility region, a constraining grid, and a Faraday disk. The above components of a conventional ion mobility tube are formed by means of separate metal electrode sheets. The electrode sheets are separated from each other by insulating material. The metal electrode sheets are connected to an external cable or separate divider resistors are welded between the metal electrode sheets, or divider resistors are disposed outside the ion mobility tube. Such an ion mobility tube has a complicated structure with many lead wires, and cannot be easily detached since two electrode sheets are welded to each other through wires or electronic elements. In addition, all the structures such as the ion door and the constraining grid are made of thin net-shaped or wire-shaped metal and thus have a bad strength in the conventional ion mobility tube. Change in performance caused by deformation is considerable, therefore accuracy of detection of the ion mobility tube is degraded.

SUMMARY OF THE INVENTION

The present invention has been made to resolve at least one of the technical problems in the prior art. Therefore, an object of the present invention is to provide an ion mobility tube which has a simplified structure and can be conveniently manufactured and detached.

An ion mobility tube according to the present invention comprises an ionization source chamber having a center ionization source chamber hole, an ion door, a mobility region unit having a center mobility tube chamber, a constraining grid, and a Faraday disk, the ionization source chamber, the ion door, the mobility region unit, the constraining grid, and the Faraday disk are laminated together in sequence in a front-rear direction, wherein the mobility region unit comprises a first insulator and first metal electrode sheets concentrically fixed to a front surface and a back surface of the first insulator respectively.

According to the mobility tube of an embodiment of the present invention, the mobility region unit comprises the first insulator and the first metal electrode sheets which are integral. Therefore, the mobility tube is advantageous in simplified manufacturing process, and convenient for detachment and assembly.

In addition, the ion mobility tube according to an embodiment of the present invention further has the following additional technical features.

The first insulator is formed with a first electronic element accommodating hole located on radial outsides of the first metal electrode sheets.

The first insulator is further formed with a first wiring hole located on the radial outsides of the first metal electrode sheets.

The ionization source chamber comprises a second insulator and second metal electrode sheets concentrically fixed to a front surface and a back surface of the second insulator respectively and connected to each other.

The second insulator is formed with a second electronic element accommodating hole located on radial outsides of the second metal electrode sheets.

The second insulator is further formed with a second wiring hole located on the radial outsides of the second metal electrode sheets.

The ionization source chamber is formed with a second electric via hole penetrating through the second insulator and the second metal electrode sheets.

The ion door comprises a third insulator and third metal electrode sheets concentrically fixed to a front surface and a back surface of the third insulator respectively.

The third insulator is formed with a third electronic element accommodating hole located on radial outsides of the third metal electrode sheets.

The third insulator is formed with a third wiring hole located on the radial outsides of the third metal electrode sheets.

The constraining grid comprises a fourth insulator, and a fourth front metal electrode sheet and a fourth back metal electrode sheet concentrically fixed to a front surface and a back surface of the fourth insulator respectively and connected to each other, wherein the fourth back metal electrode sheet is annular in shape.

The fourth insulator is formed with a fourth electronic element accommodating hole located on radial outsides of the fourth front metal electrode sheet and the fourth back metal electrode sheet.

The fourth insulator is formed with a fourth wiring hole located on the radial outsides of the fourth front metal electrode sheet and the fourth back metal electrode sheet.

The constraining grid is formed with a fourth electronic via hole penetrating through the fourth insulator to connect the fourth front metal electrode sheet and the fourth back metal electrode sheet.

The Faraday disk comprises a fifth insulator and fifth metal electrode sheets concentrically fixed to a front surface and a back surface of the fifth insulator respectively and connected to each other.

The fifth insulator is formed with a fifth electronic element accommodating hole located on radial outsides of the fifth metal electrode sheets.

The Faraday disk further comprises annular metal electrode sheets concentrically fixed to the front surface and the back surface of the fifth insulator respectively, fitted over the radial outsides of the fifth metal electrode sheets respectively, and connected to each other, wherein the fifth electronic element accommodating hole is located on radial outsides of the annular metal electrode sheets.

The fifth insulator is further formed with a fifth wiring hole located on the radial outsides of the annular metal electrode sheets.

The fifth insulator is formed with a ventilation hole located inside the annular metal electrode sheets and outside the fifth metal electrode sheets.

The Faraday disk is formed with a fifth electric via hole for connecting the annular metal electrode sheets.

The ion mobility tube according to an embodiment of the present invention further comprises a Faraday disk rear cover ring and a Faraday disk rear cover plate laminated in sequence behind the Faraday disk, the Faraday disk rear cover plate comprises a sixth insulator and sixth metal electrode sheets concentrically fixed to a front surface and a back surface of the sixth insulator respectively and connected to each other, and the Faraday disk rear cover ring comprises a seventh insulator having a seventh center hole and seventh annular metal electrode sheets concentrically fixed to a front surface and a back surface of the seventh insulator respectively.

The sixth insulator is formed with sixth wiring holes respectively located on the radial outsides of the sixth metal electrode sheets, and the seventh insulator is formed with seventh wiring holes respectively located on the radial outsides of the seventh annular metal electrode sheets.

The Faraday disk rear cover plate is formed with sixth electric via holes respectively penetrating through the sixth insulator and the sixth metal electrode sheets.

A gas nozzle is mounted on a back surface of the Faraday disk rear cover plate.

The ionization source chamber, the ion door, the mobility region unit, the constraining grid, the Faraday disk, and the Faraday disk rear cover plate are formed with mounting holes respectively, and laminated together by means of a bolt that passes through the mounting holes.

The first insulator is ceramic, and the first metal electrode sheets are formed on the first insulator by corrosion, electroplating, deposition, or spray painting, respectively.

Additional aspects and advantages of the present invention will be set forth in part in the description which follows and, in part, will be apparent from the description, or may be learned by practice of the invention.

BRIEF DESCRIPTION OF THE DRAWINGS

The above and/or additional aspects and advantages of the present invention will be apparent and more readily appreciated from the following description of embodiments taken in conjunction with the accompanying drawings, in which.

DETAILED DESCRIPTION OF THE EMBODIMENTS

Figure 1:
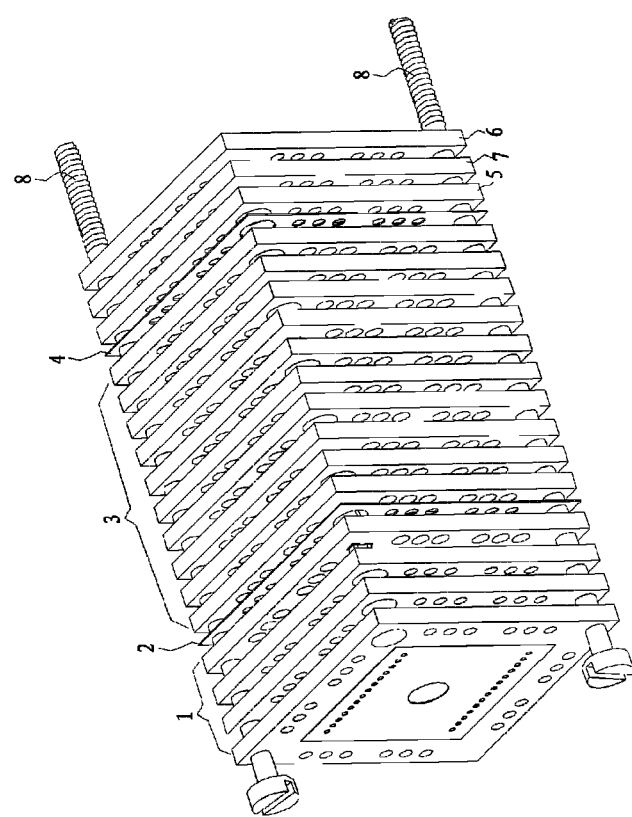
FIG. 1 is a perspective view of an ion mobility tube according to an embodiment of the present invention in an assembled state.

Reference will now be made in detail to the embodiments of the present invention, examples of which are illustrated in the accompanying drawings, wherein like reference numerals refer to like elements or elements having like function throughout. The embodiments described below with reference to the accompany drawings are illustrative, are only used to explain the present invention, and should not be construed to limit the present invention.

In the description of the present invention, orientations or positional relationships indicated by the terms such as "front", "back", "left", "right", "radial" "axial", and "rear" are based on orientations or positional relationships shown in the accompanying drawings, are merely used to facilitate the description of the present invention, but do not require that the present invention should be configured and operated in a particular orientation. Therefore, the orientations or positional relationships should not be construed to limit the present invention.

An ion mobility tube according to an embodiment of the present invention will now be described in detail with reference to the accompany drawings.

As shown FIG. 1, the ion mobility tube according to an embodiment of the present invention comprises an ionization source chamber 1, an ion door 2, a mobility region unit 3, a constraining grid 4, and a Faraday disk 5. In some embodiments of the present invention, the ion mobility tube further comprises a Faraday disk rear cover plate 6.

As shown in FIG. 1, the ionization source chamber 1, the ion door 2, the mobility region unit 3, the constraining grid 4, the Faraday disk 5, a Faraday disk rear cover ring 7, and the Faraday disk rear cover plate 6 are laminated together in sequence in a front-rear direction (a right-left direction in FIG. 1).

In the example shown in FIG. 1, the ionization source chamber 1, the ion door 2, the mobility region unit 3, the constraining grid 4, the Faraday disk 5, and the Faraday disk rear cover plate 6 are formed with mounting holes at upper left corners and lower right corners, respectively, and bolts 8 pass through the mounting holes to assemble them together in sequence in the front-rear direction.

Components of the ion mobility tube according to an embodiment of the present invention will now be described in detail with reference to the accompany drawings.

As shown in FIGS. 8-11, the mobility region unit 3 has a center mobility tube chamber 314, and comprises a first insulator 31 and first metal electrode sheets 32 concentrically fixed to a front surface (a left surface in FIG. 10) and a back surface (a right surface in FIG. 10) of the first insulator 31 respectively. The first metal electrode sheets 32 have first metal electrode sheet center holes 321 corresponding to the center mobility tube chamber 314.

The first metal electrode sheets 32 may be connected to each other through an electronic element 8. In other words, the first metal electrode sheets 32 are connected to each other through a resistor. For example, the electronic element 8 connects the first metal electrode sheets 32 on the front and back surfaces through lead wires 322 led out from the first metal electrode sheets 32 on the front and back surfaces, respectively.

In some embodiments of the present invention, the first insulator 31 is ceramic and thus has high-temperature resistance and high-voltage resistance, and the first metal electrode sheets 32 may be formed on the first insulator 31 by corrosion, electroplating, deposition, or spray painting so that the insulator 31 and the first metal electrode sheets 32 on the front and back surfaces constitute a single integral unit. Of course, the present invention is not limited to this. For example, the first insulator 31 may also be made of the same material as a common circuit board, and the first metal electrode sheets 32 are formed on the first insulator 31 as a circuit is printed on a circuit board. In the embodiment shown in FIGS. 8-10, the first insulator 31 and the first metal electrode sheets 32 are generally square in shape, but the present invention is not limited to this.

According to the embodiment of the present invention, the mobility region unit comprises the first insulator 31 and the first metal electrode sheets 32 which are integral. Therefore, the mobility region unit can be formed directly by series connection so long as mutual metal portions of the mobility region units between the mobility region units are brought into contact with each other. Hence, assembly and detachment are simply carried out and cost thereof is reduced.

Figure 11:
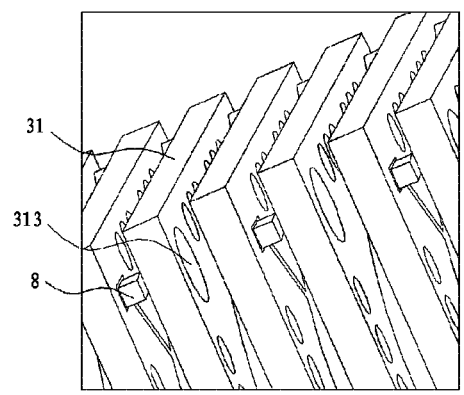
FIG. 11 is a local perspective view of a plurality of the mobility region units laminated together.
Figure 12:
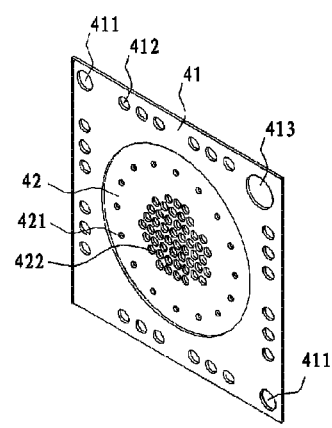
FIG. 12 is a perspective view of a constraining grid of the ion mobility tube shown in FIG. 1.

As shown in FIG. 1, a mobility region of the mobility tube may comprise a plurality of the mobility region units 3. In other words, the mobility region comprises a plurality of the first insulators 31 which are laminated together and of which the front and back surfaces are fixed with the first metal electrode sheets 32 respectively, as shown in FIG. 11. A specific number of the mobility region units 3 may be selected according to specific application. Therefore, a length of the mobility region of the mobility tube can be conveniently adjusted.

Figure 8:
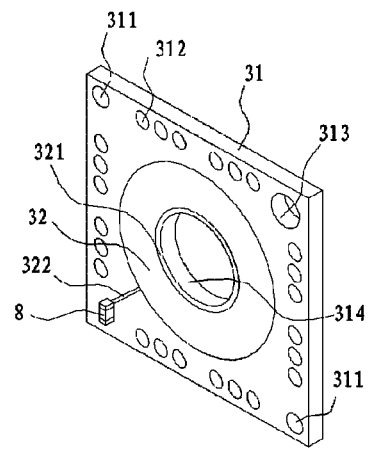
FIG. 8 is a perspective view of a mobility region unit of the ion mobility tube shown in FIG. 1.
Figures 9, 10:
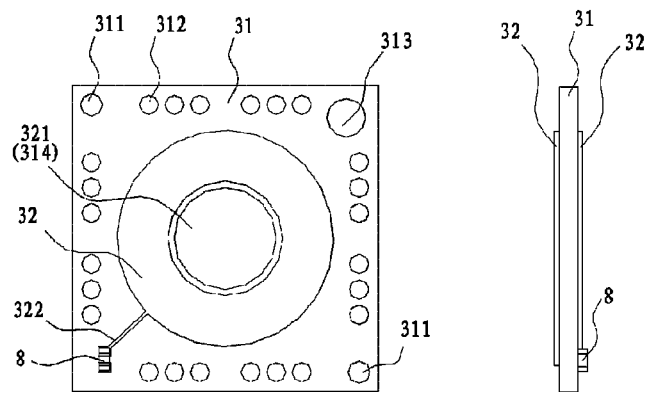
FIG. 9 is a front view of the mobility region unit shown in FIG. 8.
FIG. 10 is a side view of the mobility region unit shown in FIG. 9.

In some embodiments of the present invention, as shown in FIGS. 8-9, the first insulator 31 is formed with a first electronic element accommodating hole 313 located on radial outsides of the first metal electrode sheets 32. In the example shown in FIGS. 8-9, the first electronic element accommodating hole 313 is formed at an upper right corner of the first insulator 31. The first electronic element accommodating hole 313 is used to accommodate the electronic element 8 welded to the adjacent mobility region unit 3. As shown in FIG. 11, the first electronic element accommodating hole 313 in one of the mobility region units 3 is opposite to the electronic element 8 on the one of the mobility region units 3. Therefore, the first electronic element accommodating hole 313 in one of the mobility region units 3 is opposite to the first electronic element accommodating hole 313 in adjacent one of the mobility region units 3. Hence, when the mobility region units 3 are laminated together, the electronic element on one of the mobility region units 3 is accommodated in the first electronic element accommodating hole 313 in adjacent one of the mobility region units 3. Therefore, it is not necessary to lead out lead wires for connection to an external electronic element from the first metal electrode sheets 32. As a result, lead wires of the mobility region unit 3 are decreased, the structure thereof is simplified. It is convenient to carry out manufacture and assembly of the tube, the appearance thereof is neat, and reliability of connection of the electronic elements is improved.

As shown in FIGS. 8 and 9, in a further embodiment of the present invention, the first insulator 31 is further formed with a first wiring hole 312 which is located on the radial outsides of the first metal electrode sheets 32, and through which a cable passes, so that it is not necessary to expose the cable of the mobility tube to an outside of the mobility tube, thereby ensuring reliability of connection, neat appearance, and convenient connection. In the example shown in FIGS. 8 and 9, the first wiring hole 312 is formed at a peripheral edge of the first insulator 31. The first insulator 31 is formed with mounting holes 311 at an upper left corner and a lower right corner, respectively, and the bolts 8 pass through the mounting holes to laminate the mobility region units 3 and the other components of the mobility tube together in sequence to form the ion mobility tube.

The ionization source chamber 1 of the ion mobility tube according to an embodiment of the present invention will now be described with reference to FIGS. 2-4.

The ionization source chamber 1 has a ionization source chamber center hole, and the ionization source chamber 1 comprises a second insulator 11 and second metal electrode sheets 12 concentrically fixed to a front surface (a left surface in FIG. 4) and a back surface (a right surface in FIG. 4) of the second insulator 11 respectively and connected to each other. The insulator 11 has a second insulator center hole 114, and accordingly the second metal electrode sheets 12 have second metal electrode sheet center holes 121.

Figure 2:
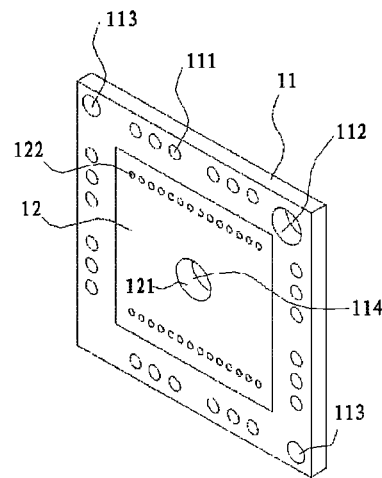
FIG. 2 is a perspective view of an ionization source chamber of the ion mobility tube shown in FIG. 1.
Figures 3, 4:
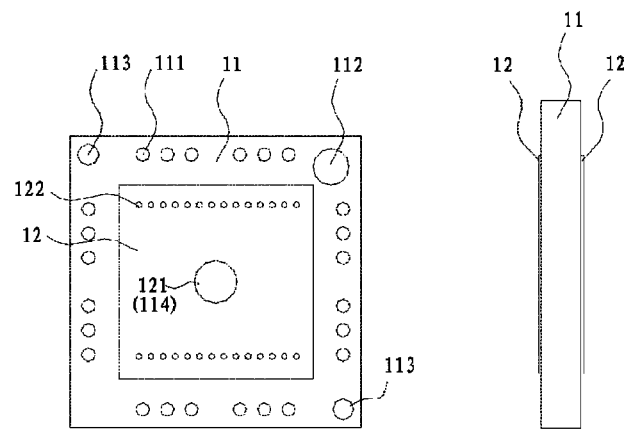
FIG. 3 is a front view of the ionization source chamber shown in FIG. 2.
FIG. 4 is a side view of the ionization source chamber shown in FIG. 3.

As shown in FIGS. 2 and 3, the second insulator 11 is provided with mounting holes 113 at an upper left corner and a lower right corner, respectively, and the bolts 8 pass through the mounting holes to laminate the ionization source chamber 3 and the other components of the mobility tube together.

Like the mobility region unit 3, the second insulator 11 may also be ceramic, and the second metal electrode sheets 12 may be formed on the second insulator 12 by corrosion, electroplating, deposition, or spray painting. In addition, the second insulator 11 may also be made of the same material as a common circuit board, and the second metal electrode sheets 12 are formed on the second insulator 11 as a circuit is printed on a circuit board.

As shown in FIGS. 2 and 3, the second insulator 11 is formed with a second electronic element accommodating hole 112 located on radial outsides of the second metal electrode sheets 12. More specifically, the second electronic element accommodating hole 112 is formed at an upper right corner of the second insulator 11 to accommodate the electronic element. The second insulator 11 and the second metal electrode sheets 12 have a generally square shape in the example shown in FIGS. 2 and 3, but the present invention is not limited to this.

In some embodiments of the present invention, as shown in FIGS. 2 and 3, the second insulator 11 is further formed with a second wiring hole 111 located on the radial outsides of the second metal electrode sheets 12. A cable passes through the second wiring hole 111 which is similar to the first wiring hole 312. After the mobility tube is assembled, the second wiring hole 111 is aligned with the first wiring hole 312.

In the example shown in FIGS. 2 and 3, the ionization source chamber 1 is formed with a second electric via hole 122 penetrating through the second insulator 11 and the second metal electrode sheets 12. The second electric via hole 122 is used to connect the second metal electrode sheets 12 located on the front and back surfaces of the second insulator 11. It should be appreciated that connection of the second metal electrode sheets 12 on the front and back surfaces of the second insulator 11 is not limited to the connection performed by the second electric via hole 122. For example, the second metal electrode sheets 12 on both sides may also be connected through metal disposed within the center holes of the second insulator 11 and the second metal electrode sheets 12.

The ion door 2 of the ion mobility tube according to an embodiment of the present invention will now be described with reference to FIGS. 5-7.

Figure 5:
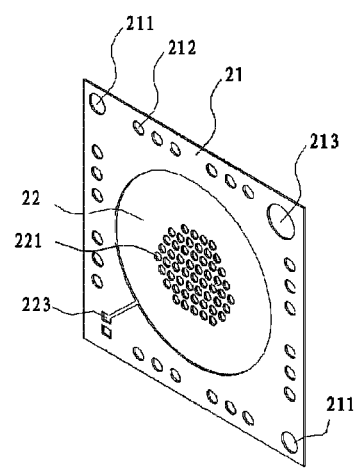
FIG. 5 is a perspective view of an ion door of the ion mobility tube shown in FIG. 1.
Figure 6:
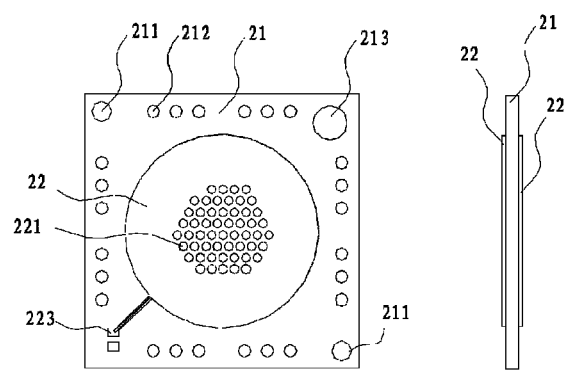
FIG. 6 is a front view of the ion door shown in FIG. 5.
Figure 7:
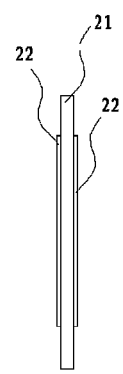
FIG. 7 is a side view of the ion door shown in FIG. 6.

As shown in FIGS. 5-7, the ion door 2 comprises a third insulator 21 and third metal electrode sheets 22 concentrically fixed to a front surface and a back surface of the third insulator 21 respectively. The third insulator 21 may be e.g. ceramic, and the third metal electrode sheets 22 may be fixed to the front surface and the back surface of the third insulator 21 in the above appropriate manners.

The third insulator 21 is formed with a third electronic element accommodating hole 213 located on radial outsides of the third metal electrode sheets 22. In FIG. 6, for example, the third electronic element accommodating hole 213 is formed at an upper right corner of the third insulator 21 to accommodate the electronic element. For example, the electronic element is connected to the third metal electrode sheets 22 on the front and back surfaces through lead wires 223 led out from the third metal electrode sheets 22 on the front and back surfaces of the third insulator 21, respectively, so as to connect the two third metal electrode sheets 22 on the front and back surfaces. The third insulator 21 is formed with mounting holes 211 at an upper left corner and a lower right corner, respectively, and the bolts 8 pass through the mounting holes. Similarly, the third insulator 21 is formed with a third wiring hole 212 located on the radial outsides of the third metal electrode sheets 22. A cable passes through the third wiring hole 212.

The third metal electrode sheets 22 on the front and back surfaces of the third insulator 21 are formed with ion passage holes 221 and accordingly the third insulator 21 is also formed with a ion passage hole aligned with the ion passage holes 221 so that ions may pass through the ion passage holes, which is similar to prior art and is not further described in detail.

The constraining grid 4 of the ion mobility tube according to an embodiment of the present invention will now be described with reference to FIGS. 13 and 14.

The constraining grid 4 comprises a fourth insulator 41, and a fourth front metal electrode sheet 42 and a fourth back metal electrode sheet 43 concentrically fixed to a front surface and a back surface of the fourth insulator 41 respectively and connected to each other. The fourth back metal electrode sheet 43 is annular in shape. Like the first, second and three insulators, the fourth insulator 41 is formed with a fourth electronic element accommodating hole 413 located on radial outsides of the fourth front metal electrode sheet 42 and the fourth back metal electrode sheet 43 to accommodate the electronic element. In a further embodiment, the fourth insulator 41 is formed with a fourth wiring hole 412 located on the radial outsides of the fourth front metal electrode sheet 42 and the fourth back metal electrode sheet 43. The cable passes through the fourth wiring hole 412. In addition, the fourth insulator 41 is further formed with mounting holes 411, and the bolts 8 pass through the mounting holes 411.

Figure 13:
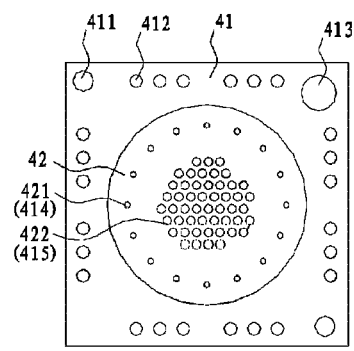
FIG. 13 is a front view of the constraining grid shown in FIG. 12.
Figure 14:
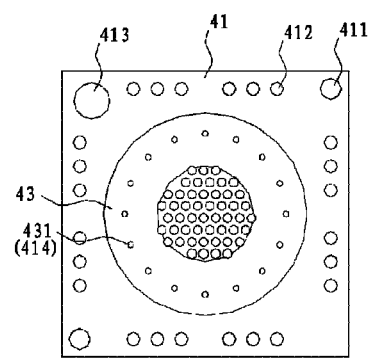
FIG. 14 is a rear view of the constraining grid shown in FIG. 13.

As shown in FIGS. 13 and 14, the fourth insulator 41 is formed with a fourth electronic via hole 421 penetrating through the fourth insulator 41 to connect the fourth front metal electrode sheet 42 and the fourth back metal electrode sheet 43. Accordingly, the fourth insulator 41 may be formed with a corresponding via hole 414. The fourth electronic via hole 421 is used to connect the fourth front metal electrode sheet 42 and the fourth back metal electrode sheet 43, but the present invention is not limited to this.

Like the ion door 2, the fourth front metal electrode sheet 42 is formed with an ion passage hole 422 and accordingly the fourth insulator 4 is formed with a passage hole 415 so that ions pass through the passage holes, which is similar to prior art and is not further described in detail.

As shown in FIGS. 13 and 14, the fourth front metal electrode sheet 42 is generally circular in shape, and the ion passage hole 422 is formed in a center portion of the fourth front metal electrode sheet. The fourth back metal electrode sheet 43 is annular in shape, and the ion passage hole 422 and the passage hole 415 are formed inside a center hole of the fourth back metal electrode sheet 43.

The fourth insulator 41 may also be ceramic, and the fourth front metal electrode sheet 42 and the fourth back metal electrode sheet 43 may be formed and fixed on the fourth insulator 41 in the above appropriate manners.

The Faraday disk 5 of the ion mobility tube according to an embodiment of the present invention will now be described with reference to FIGS. 15 and 16.

Figure 15:
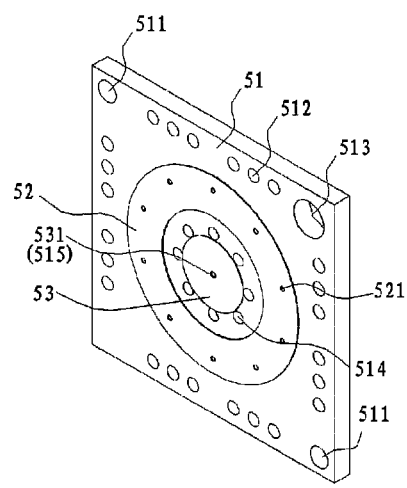
FIG. 15 is a perspective view of a Faraday disk of the ion mobility tube shown in FIG. 1.
Figure 16:
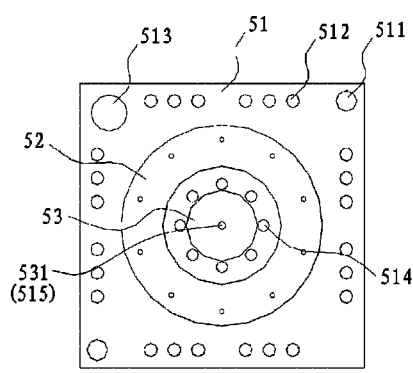
FIG. 16 is a front view of the Faraday disk shown in FIG. 15.

As shown in FIGS. 15 and 16, the Faraday disk 5 comprises a fifth insulator 51 and fifth metal electrode sheets 53 concentrically fixed to a front surface and a back surface of the fifth insulator 51 respectively and connected to each other. The fifth insulator 51 is formed with a fifth electronic element accommodating hole 513 located on radial outsides of the fifth metal electrode sheets 53 to accommodate the electronic element. In addition, the fifth insulator 51 is further formed with mounting holes 511, and the bolts 8 pass through the mounting holes.

The Faraday disk 5 further comprises annular metal electrode sheets 53 concentrically fixed to the front surface and the back surface of the fifth insulator 51 respectively, fitted over the radial outsides of the fifth metal electrode sheets 53 respectively, and connected to each other. The fifth electronic element accommodating hole 513 is located on radial outsides of the annular metal electrode sheets 52. A fifth wiring hole 512 is formed in the fifth insulator 51 on the radial outsides of the annular metal electrode sheets 52. The cable passes through the fifth wiring hole 512. The Faraday disk 5 may also be formed with a fifth electric via hole 521 for connecting the annular metal electrode sheets 52. The fifth metal electrode sheets 53 may be connected to each other through a center hole 531, and accordingly a center hole 515 is formed in the fifth insulator 51. As shown in FIGS. 15 and 16, the fifth insulator 51 is formed with a first ventilation hole 514 between the fifth metal electrode sheets 53 and the annular metal electrode sheets 52 to introduce air into the mobility tube.

The fifth insulator 51 may be ceramic, and the fifth metal electrode sheets 53 and the annular metal electrode sheets 52 may be formed and fixed on the fifth insulator 51 in the above appropriate manners.

The Faraday disk rear cover ring 7 and Faraday disk rear cover plate 6 of the ion mobility tube according to an embodiment of the present invention will now be described with reference to FIGS. 17 and 18. The Faraday disk rear cover plate 6 comprises a sixth insulator 61 and sixth metal electrode sheets 62 concentrically fixed to a front surface and a back surface of the sixth insulator 61 respectively and connected to each other. The sixth insulator 61 is formed with mounting holes 611, and the bolts 8 pass through the mounting holes 611. The sixth insulator 61 is formed with sixth wiring holes 621 respectively located on radial outsides of the sixth metal electrode sheets 62. The cable passes through the sixth wiring holes. The Faraday disk rear cover plate 6 is formed with sixth electric via holes 621 (the corresponding electric via hole in the sixth insulator 61 is indicated by 613) respectively penetrating through the sixth insulator 61 and the sixth metal electrode sheets 62 to connect the sixth metal electrode sheets 62 on both sides of the sixth insulator 61.

Figure 17:
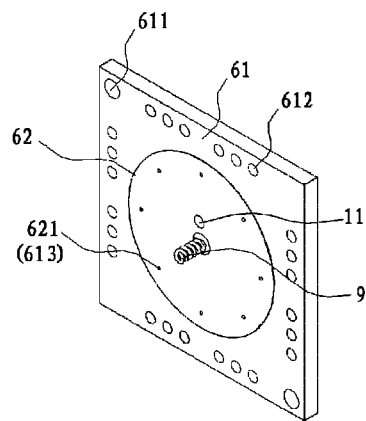
FIG. 17 is a front perspective view of a Faraday disk rear cover plate of the ion mobility tube shown in FIG. 1.
Figure 18:
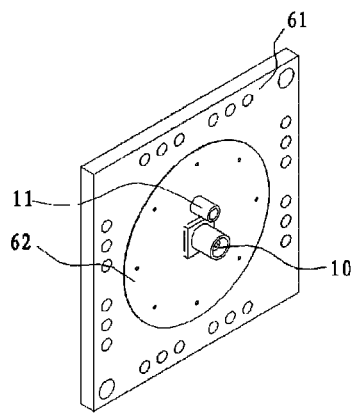
FIG. 18 is a rear perspective view of the Faraday disk rear cover plate of the ion mobility tube shown in FIG. 1.

As shown in FIGS. 17 and 18, a spring 9 may be mounted at a center portion of the sixth insulator 61 to be in contact with the fifth metal electrode sheets 53 of the Faraday disk 5. A gas nozzle is mounted on a back surface of the six insulator 61 to ventilate an inside of the mobility tube through the ventilation hole.

The sixth insulator 61 may also be ceramic, and the sixth metal electrode sheets 62 may be formed and fixed on the front surface and the back surface of the sixth insulator 61 in the above appropriate manners.

Figure 19:
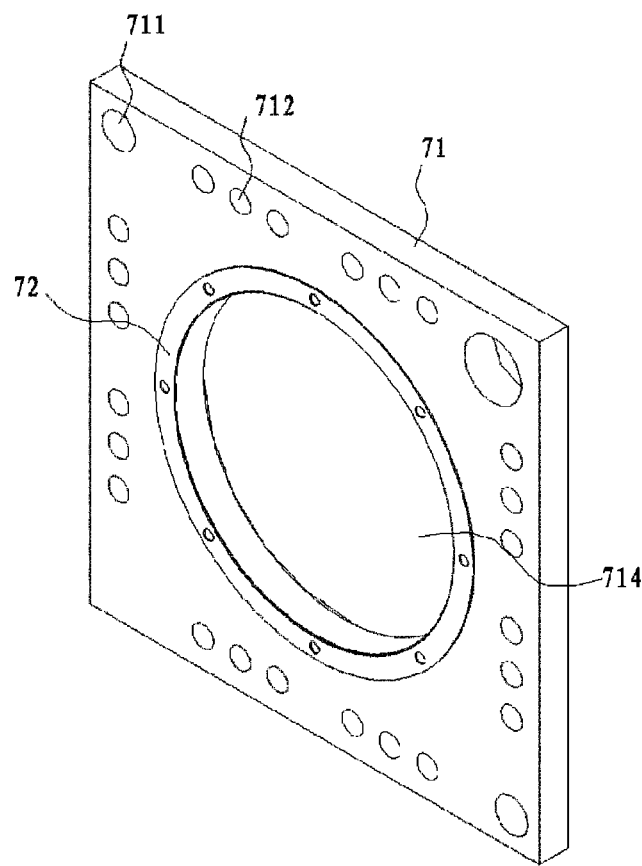
FIG. 19 is a front perspective view of a Faraday disk rear cover ring of the ion mobility tube shown in FIG. 1.

As shown in FIGS. 1 and 19, the Faraday disk rear cover ring 7 is disposed between the Faraday disk rear cover plate 6 and the Faraday disk 5 to provide the spring 9 with a stroke space so as to ensure good contact. Specifically, the Faraday disk rear cover ring 7 comprises a seventh insulator 71 having a center hole 714, and seventh annular metal electrode sheets 72 disposed on a front surface and a back surface of the seventh insulator respectively. Mounting holes 711 is formed through the seventh insulator 71 on radial outsides of the seventh annular metal electrode sheets 72, and the bolts 8 pass through the mounting holes. For example, the mounting holes 711 are formed at an upper left corner and a lower right corner of the seventh insulator 71. The seventh insulator 71 is further formed with a seventh wiring hole 721 located on the radial outsides of the seventh annular metal electrode sheets 72. The cable passes through the seventh wiring hole.

According to the ion mobility tube of the embodiment of the present invention, the ionization source chamber 1, the ion door 2, the mobility region unit 3, the constraining grid 4, the Faraday disk 5, and the Faraday disk rear cover plate 6 may be laminated together in sequence by means of the bolts 8, and each of the above members is an integral unit composed of an insulator and metal electrode sheets, the electronic elements may be accommodated in the corresponding electronic element accommodating holes, and thus external lead wires and externally linked electronic elements are not needed and the cable can pass through the mobility tube through the wiring holes. Therefore, the mobility tube according to the present invention is advantageous in simplified manufacturing, convenient for assembly and detachment, and has a neat appearance, high reliability and accuracy of detection.

While the embodiments of the present invention has been shown and described, it will be understood by those skilled in the art that various changes, modifications, substitutions and alterations may be made therein without departing from the principles and spirit of the present invention, the scope of which is defined in the appended claims and their equivalents.

The invention claimed is:

1. An ion mobility tube, comprising: an ionization source chamber having a center ionization source chamber hole, an ion door, a mobility region unit having a center mobility tube chamber, a constraining grid, and a Faraday disk, and the ionization source chamber, the ion door, the mobility region unit, the constraining grid, and the Faraday disk are laminated together in sequence in a front-rear direction, wherein the mobility region unit comprises a first insulator and first metal electrode sheets concentrically fixed to a front surface and a back surface of the first insulator respectively.

2. The ion mobility tube of claim 1, characterized in that the first insulator is formed with a first electronic element accommodating hole located on radial outsides of the first metal electrode sheets.

3. The ion mobility tube of claim 2, characterized in that the first insulator is further formed with a first wiring hole located on the radial outsides of the first metal electrode sheets.

4. The ion mobility tube of claim 1, characterized in that the ionization source chamber comprises a second insulator and second metal electrode sheets concentrically fixed to a front surface and a back surface of the second insulator respectively and connected to each other.

5. The ion mobility tube of claim 4, characterized in that the second insulator is formed with a second electronic element accommodating hole located on radial outsides of the second metal electrode sheets.

6. The ion mobility tube of claim 5, characterized in that the second insulator is further formed with a second wiring hole located on the radial outsides of the second metal electrode sheets.

7. The ion mobility tube of claim 6, characterized in that the ionization source chamber is formed with a second electric via hole penetrating through the second insulator and the second metal electrode sheets.

8. The ion mobility tube of claim 1, characterized in that the ion door comprises a third insulator and third metal electrode sheets concentrically fixed to a front surface and a back surface of the third insulator respectively.

9. The ion mobility tube of claim 8, characterized in that the third insulator is formed with a third electronic element accommodating hole located on radial outsides of the third metal electrode sheets.

10. The ion mobility tube of claim 9, characterized in that the third insulator is formed with a third wiring hole located on the radial outsides of the third metal electrode sheets.

11. The ion mobility tube of claim 1, characterized in that the constraining grid comprises a fourth insulator, and a fourth front metal electrode sheet and a fourth back metal electrode sheet concentrically fixed to a front surface and a back surface of the fourth insulator respectively and connected to each other, and the fourth back metal electrode sheet is annular in shape.

12. The ion mobility tube of claim 11, characterized in that the fourth insulator is formed with a fourth electronic element accommodating hole located on radial outsides of the fourth front metal electrode sheet and the fourth back metal electrode sheet.

13. The ion mobility tube of claim 12, characterized in that the fourth insulator is formed with a fourth wiring hole located on the radial outsides of the fourth front metal electrode sheet and the fourth back metal electrode sheet.

14. The ion mobility tube of claim 13, characterized in that the constraining grid is formed with a fourth electronic via hole penetrating through the fourth insulator to connect the fourth front metal electrode sheet and the fourth back metal electrode sheet.

15. The ion mobility tube of claim 1, characterized in that the Faraday disk comprises a fifth insulator and fifth metal electrode sheets concentrically fixed to a front surface and a back surface of the fifth insulator respectively and connected to each other.

16. The ion mobility tube of claim 15, characterized in that the fifth insulator is formed with a fifth electronic element accommodating hole located on radial outsides of the fifth metal electrode sheets.

17. The ion mobility tube of claim 16, characterized in that the Faraday disk further comprises annular metal electrode sheets concentrically fixed to the front surface and the back surface of the fifth insulator respectively, fitted over the radial outsides of the fifth metal electrode sheets respectively, and connected to each other, wherein the fifth electronic element accommodating hole is located on radial outsides of the annular metal electrode sheets.

18. The ion mobility tube of claim 17, characterized in that the fifth insulator is further formed with a fifth wiring hole located on the radial outsides of the annular metal electrode sheets.

19. The ion mobility tube of claim 18, characterized in that the fifth insulator is formed with a ventilation hole located inside the annular metal electrode sheets and outside the fifth metal electrode sheets.

20. The ion mobility tube of claim 19, characterized in that the Faraday disk is formed with a fifth electric via hole for connecting the annular metal electrode sheets.

21. The ion mobility tube of claim 1, characterized in that it further comprises a Faraday disk rear cover ring and a Faraday disk rear cover plate laminated in sequence behind the Faraday disk, the Faraday disk rear cover plate comprises a sixth insulator and sixth metal electrode sheets concentrically fixed to a front surface and a back surface of the sixth insulator respectively and connected to each other, and the Faraday disk rear cover ring comprises a seventh insulator having a seventh center hole and seventh annular metal electrode sheets concentrically fixed to a front surface and a back surface of the seventh insulator respectively.

22. The ion mobility tube of claim 21, characterized in that the sixth insulator is formed with sixth wiring holes respectively located on radial outsides of the sixth metal electrode sheets, and the seventh insulator is formed with seventh wiring holes respectively located on radial outsides of the seventh annular metal electrode sheets.

23. The ion mobility tube of claim 22, characterized in that the Faraday disk rear cover plate is formed with sixth electric via holes respectively penetrating through the sixth insulator and the sixth metal electrode sheets.

* * * * *